United States Patent [19]
Mather et al.

[11] 3,990,448
[45] Nov. 9, 1976

[54] ENEMA TIP

[75] Inventors: Byron L. Mather, Milwaukee; Wylie J. Dodds, Brookfield, both of Wis.

[73] Assignee: Plastronics, Inc., Milwaukee, Wis.

[22] Filed: Feb. 23, 1976

[21] Appl. No.: 660,077

Related U.S. Application Data

[63] Continuation of Ser. No. 500,262, Aug. 26, 1974, abandoned.

[52] U.S. Cl. .............................................. 128/239
[51] Int. Cl.² ......................................... A61M 3/00
[58] Field of Search .......... 128/239, 227, 245, 224, 128/241, 261, 341

[56] References Cited
UNITED STATES PATENTS

| | | | |
|---|---|---|---|
| 988,120 | 3/1911 | Lott | 128/341 |
| 1,149,971 | 8/1915 | Wagoner | 128/241 |
| 1,198,742 | 9/1916 | Meinecke | 128/239 |
| 1,947,150 | 2/1934 | Bacon | 128/239 |
| 3,459,175 | 8/1969 | Miller | 128/239 X |
| 3,575,160 | 4/1971 | Vass et al. | 128/245 |
| 3,828,774 | 8/1974 | Vass | 128/239 |
| 3,894,539 | 7/1975 | Tallent | 128/261 |

*Primary Examiner*—John D. Yasko
*Attorney, Agent, or Firm*—Michael, Best & Friedrich

[57] ABSTRACT

An enema tip comprising an acorn portion at the end thereof, a distal staff portion connected to the acorn portion and a stop or locator portion connected to the distal staff. The acorn portion has a rounded tip which tapers to a head portion and a retainer shoulder formed adjacent the head portion. The locator portion is of a diameter greater than the distal shaft and is provided with a locating shoulder spaced approximately one inch from the retainer shoulder on the acorn tip.

1 Claim, 3 Drawing Figures

U.S. Patent  Nov. 9, 1976  3,990,448
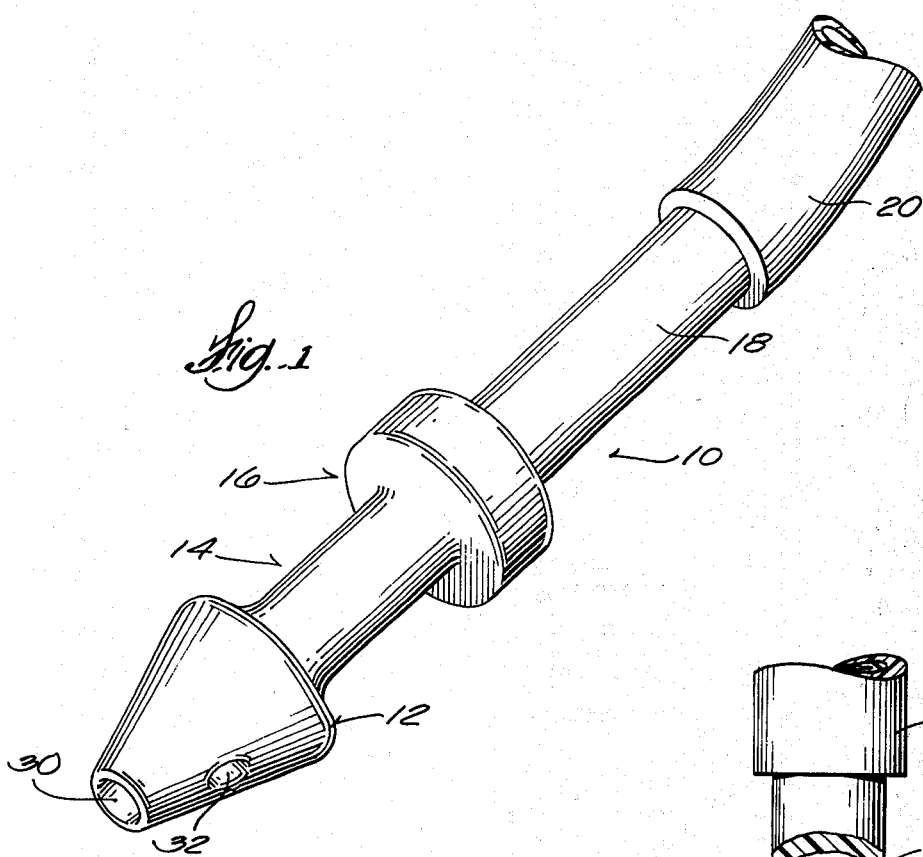
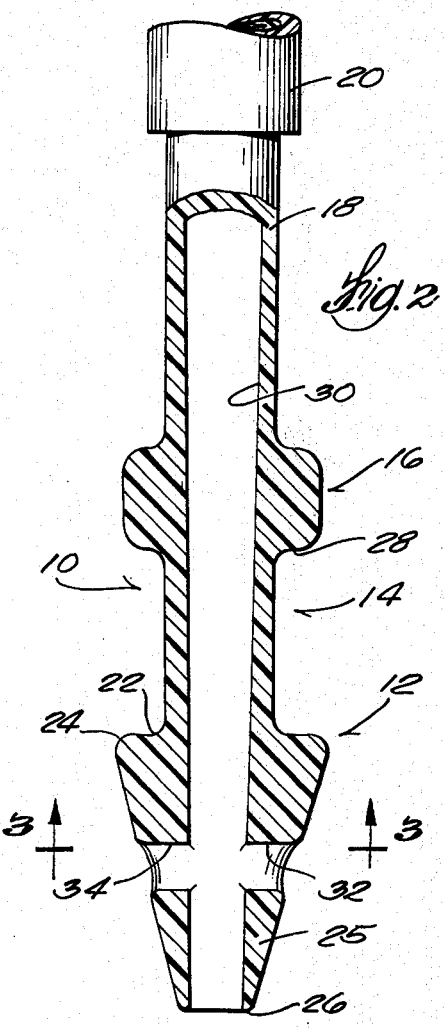
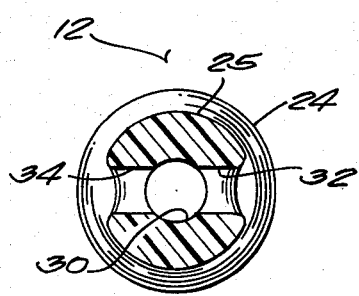

ENEMA TIP

This is a continuation of application Ser. No. 500,262, filed Aug. 26, 1974, now abandoned.

BACKGROUND OF THE INVENTION

1. Field of the Invention

This invention relates to enema tip and more particularly to an enema tip designed for introduction of a barium enema into a patient.

2. Description of the Prior Art

The principal advantages of the enema tip of this invention over prior configurations known to applicants are the provisions in the tip construction for proper location and retention of the acorn tip in the patient. More specifically, the tip construction itself provides a locating feature to thus make it unnecessary for the user to perform this function.

SUMMARY OF THE INVENTION

An enema tip having a central passageway located on the horizontal axis thereof comprising an acorn portion having a smoothly rounded tip at the end thereof and a tapered surface extending from the tip to a smoothly rounded head portion. A retaining shoulder is formed on the acorn portion and extends substantially transversely of the axis of the tip immediately to the rear of the head portion. The acorn portion has at least one transverse port which communicates with the central passageway of the enema tip. A distal shaft portion having a diameter less than that of the head of the acorn portion is connected at one end to the acorn tip and has a locator portion connected to the other end thereof. The locator portion has a locating shoulder formed thereon which extends substantially transversely of the axis of the enema tip immediately adjacent the distal shaft.

DESCRIPTION OF THE DRAWINGS

FIG. 1 is a perspective view of the improved enema tip of the present invention;

FIG. 2 is a side view of the enema tip showing FIG. 1 with a part of the tip shown in sections; and FIG. 3 is a sectional view taken along line 3—3 of FIG. 2.

DESCRIPTION OF THE PREFERRED EMBODIMENT

Referring to the drawings in detail, the enema tip 10 of the present invention is comprised of three basic portions, namely, an acorn portion 12, a distal staff portion 14 and a stop or locator portion 16. The tip 10 is mounted on the end of a shaft member 18 which in turn is connected to a flexible tube 20 for connection to an enema bag (not shown). In the preferred embodiment portions 12, 14 and 16 and shaft 18 are made integral with each other out of any suitable material such as polyethylene.

Acorn portion 12 of tip 10 is comprised of a retainer shoulder 22, a head portion 24, a tapered surface 25 and a smoothly rounded tip portion 26.

Locator portion 16 is of a diameter greater than that of staff portion 14 and is provided with a locating shoulder 28. The tip 10 is provided with a central passageway 30 which extends from one end of the tip to the other and is further provided with transverse ports 32, 34 as in acorn portion 12 which communicate with central passageway 30.

In use the tapered acorn portion 12 of the enema tip is inserted into the patient's rectum. The proper degree of insertion is determined by locating shoulder 28. The diameter of head portion 24 is made large enough to prevent expulsion of the acorn portion 12 from the rectum. The optimal diameter of portion 24 is ⅞ths of an inch.

The length of shaft portion 14 between retaining shoulder 22 of acorn 12 and locating shoulder 28 of which locator portion 16 should be sufficient to accommodate the anal sphincter muscle of the average patient. The optimal distance between shoulder 22 and shoulder 28 is one inch. The provision for a locating shoulder 28 and its proper positional relationship with respect to acorn 12 is important to prevent over-insertion of the acorn tip and also to insure proper anal seating of the enema tip in the patient. The longitudinal length of locator portion 16 is not critical.

We claim:

1. An enema tip having a central passageway located on the horizontal axis thereof comprising:
    an acorn portion comprising a smoothly rounded tip at the end thereof, a tapered surface extending from said tip to a smoothly rounded head portion and a retainer shoulder extending substantial transversely of the axis of the enema tip immediately to the rear of said head portion, said acorn portion having at least one transverse port which communicates with the central passageway, the diameter of said head portion being approximately ⅞ of an inch;
    a distal shaft portion connected at one end of said acorn tip and having a diameter less than that of the head portion of said acorn portion;
    a locator portion connected to the other end of said distal shaft portion and having a locating shoulder formed thereon, said locating shoulder extending substantially transversely of the axis of the enema tip immediately adjacent said distal shaft portion, with the distance between said retainer shoulder and said locating shoulder being approximately 1 inch; and a shaft portion connected at one end to said locator portion and adapted for connection to a flexible tube at the other end, said shaft portion serving as a handle for manipulating the enema tip, said acorn portion, said distal shaft portion, said locator portion and said shaft portion being made of a semi-rigid plastic material and formed integrally with each other to provide a one piece construction.

* * * * *